(12) United States Patent
Blanchard

(10) Patent No.: US 11,845,922 B2
(45) Date of Patent: Dec. 19, 2023

(54) CELL INCUBATOR AND A TOOL FOR USE IN A CELL INCUBATOR

(71) Applicant: THRIVE BIOSCIENCE, INC., Wakefield, MA (US)

(72) Inventor: Alan Blanchard, Middleton, MA (US)

(73) Assignee: THRIVE BIOSCIENCE, INC., Wakefield, MA (US)

( * ) Notice: Subject to any disclaimer, the term of this patent is extended or adjusted under 35 U.S.C. 154(b) by 610 days.

(21) Appl. No.: 16/629,415

(22) PCT Filed: Jul. 3, 2018

(86) PCT No.: PCT/US2018/040703
§ 371 (c)(1),
(2) Date: Jan. 8, 2020

(87) PCT Pub. No.: WO2019/014017
PCT Pub. Date: Jan. 17, 2019

(65) Prior Publication Data
US 2020/0140803 A1 May 7, 2020

Related U.S. Application Data

(60) Provisional application No. 62/530,406, filed on Jul. 10, 2017.

(51) Int. Cl.
| | |
|---|---|
| C12M 1/00 | (2006.01) |
| C12M 1/04 | (2006.01) |
| C12M 1/26 | (2006.01) |
| C12M 1/36 | (2006.01) |
| C12M 1/42 | (2006.01) |

(52) U.S. Cl.
CPC ............ *C12M 41/14* (2013.01); *C12M 23/24* (2013.01); *C12M 33/04* (2013.01); *C12M 35/04* (2013.01); *C12M 41/48* (2013.01)

(58) Field of Classification Search
CPC ...... C12M 41/14; C12M 23/24; C12M 33/04; C12M 35/04; C12M 41/48
See application file for complete search history.

(56) References Cited

U.S. PATENT DOCUMENTS

| | | | | |
|---|---|---|---|---|
| 2006/0199265 | A1* | 9/2006 | Wolf | A61L 27/16 435/395 |
| 2013/0130369 | A1* | 5/2013 | Wilson | G01F 23/26 435/289.1 |
| 2015/0017711 | A1 | 1/2015 | Bennett et al. | |

(Continued)

FOREIGN PATENT DOCUMENTS

| | | |
|---|---|---|
| JP | 2016/073305 A | 5/2016 |
| WO | 2016/161155 A2 | 10/2016 |

(Continued)

*Primary Examiner* — Liban M Hassan
(74) *Attorney, Agent, or Firm* — Norris Mclaughlin, P.A.

(57) ABSTRACT

At least one tool removably mountable on a cell incubator mandrel or a cell incubator having at least one mandrel having an end portion, the at least one mandrel mounted on a movable transport for moving the at least one mandrel and at least one tool removably mountable on the end portion of the at least one mandrel. The at least one tool is preferably electrically powered and controllable by signals applied to the at least one tool to perform at least one operation with respect to the incubation of cells.

26 Claims, 5 Drawing Sheets

(56) References Cited

U.S. PATENT DOCUMENTS

2015/0337252 A1    11/2015  Martin et al.
2015/0338428 A1*   11/2015  Holmes .................. G01N 33/62
                                                        422/65

FOREIGN PATENT DOCUMENTS

| WO | 2016/161163 A2 | 10/2016 |
| WO | 2016/161169 A2 | 10/2016 |
| WO | 2016/161174 A1 | 10/2016 |
| WO | 2016/170623 A1 | 10/2016 |
| WO | 2017/079682 A1 | 5/2017 |
| WO | 2017/079692 A1 | 5/2017 |
| WO | 2017/087774 A1 | 5/2017 |

* cited by examiner

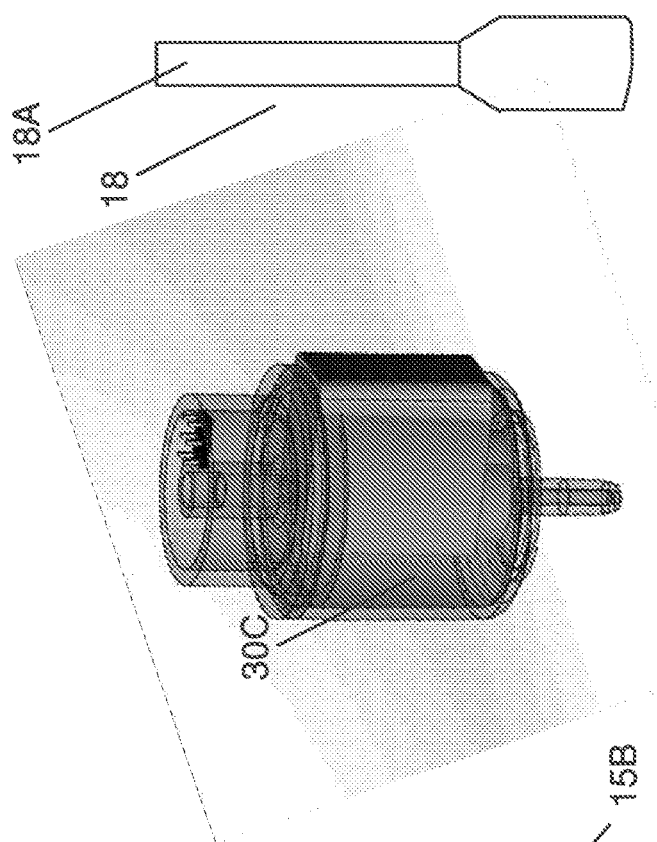
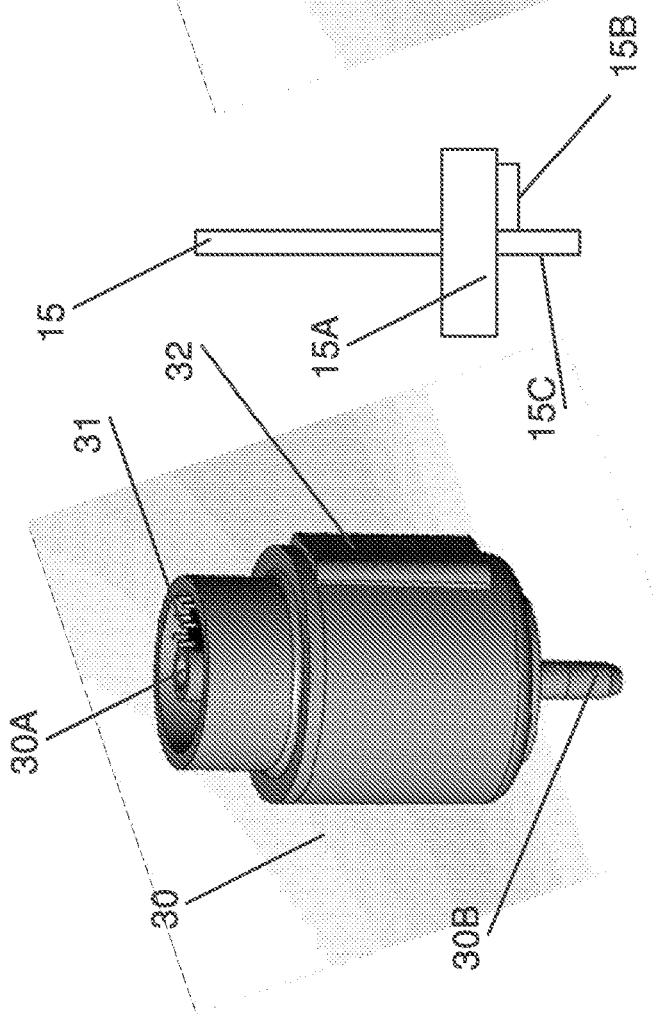
Figure 5  Figure 6  Figure 7  Figure 8

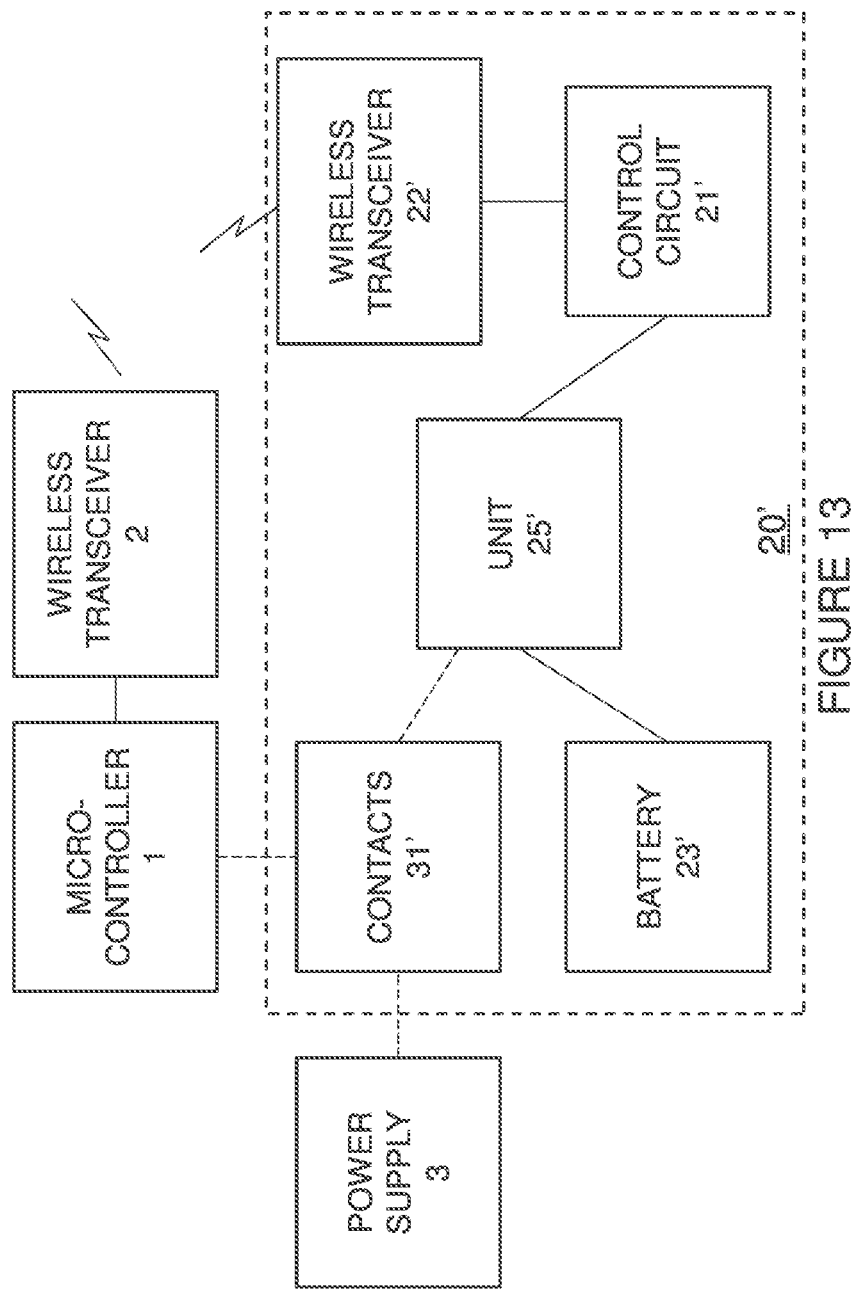

CELL INCUBATOR AND A TOOL FOR USE IN A CELL INCUBATOR

This application is a 371 of PCT/US2018/040703, filed Jul. 3, 2018, which claims priority benefit under 35 U.S.C. § 119 of the U.S. Provisional Patent Application No. 62/530,406, filed Jul. 10, 2017, the disclosures of which are incorporated herein by reference.

BACKGROUND OF THE INVENTION

The present invention relates to cell incubators and in particular to a new type of tool for use with the cell incubator.

Current cell incubators perform various operations on cells in furtherance of the incubation thereof. The cells are disposed, for example, in a culture vessel in the incubator and various tools are used to perform operations on the cells. The culture vessel is in an incubator housing that is temperature and humidity controlled, as disclosed, for example, in application WO2016161155A2 filed Mar. 31, 2016 and incorporated herein by reference and PCT/US2016/060710 filed Nov. 4, 2016. For the purposes of this application, the culture vessel is the main vessel holding the culture or a vessel holding a sample from the main vessel.

SUMMARY OF THE INVENTION

One object of the present invention is to eliminate the disadvantages of known cell incubators by improving the functionality of the tools. Preferably this is achieved by improving the incubator itself and/or to provide an improved tool that can work with existing incubators. Another object of the present invention is to provide a tool that can be retrofitted to existing incubators or can be used on incubators designed therefor to provide improved functionality.

These and other objects are achieved in accordance with the present invention by at least one tool removably mountable on a cell incubator mandrel or a cell incubator comprising at least one mandrel having an end portion, the at least one mandrel mounted on a movable transport for moving the at least one mandrel and at least one tool removably mountable on the end portion of the at least one mandrel, wherein the at least one tool is electrically powered and controllable by signals applied to the at least one tool to perform at least one operation with respect to the incubation of cells. These and other objects of the present invention are also achieved by a tool comprising a top portion for connecting to a mandrel, a reservoir connected to the top portion and a pipette tip fluidly connected to the reservoir.

In accordance with the present invention a cell incubator comprises a housing for holding a culture vessel, at least one mandrel having an end portion, the at least one mandrel mounted on a movable transport for moving the at least one mandrel relative to the culture vessel. The mandrel can be moved to a position over the culture vessel, the tool can be moved into contact with the cell culture in the vessel, or the tool can be move to a culture vessel holding a sample taken from a main culture vessel. The at least one tool is removably mountable on the end portion of the at least one mandrel, and wherein the at least one tool is electrically powered and controllable by signals applied to the at least one tool to perform at least one operation on cells in or from the culture vessel, e.g., cells that have been sampled from a main culture vessel.

The at least one tool preferably includes a battery for providing electrical energy, at least one energizable unit powered by the battery for performing an operation related to the incubation of cells and a control circuit for applying control signals to the at least one energizable unit to control the operation of the energizable unit. Alternatively, preferably, the at least one tool includes electrical contacts for mating with contacts on the mandrel for receiving at least one of electrical energy and control signals and wherein the at least one energizable unit receives at least one of the electrical energy and control signals from the contacts for performing an operation related to the incubation of cells.

In another embodiment, the at least one tool further comprises a wireless receiver for receiving control signals from externally of the tool. In another embodiment, the transport moves at least one mandrel in an X-Y plane and moves the at least one mandrel along a Z-axis when a desired position is reached in the X-Y plane.

In a further embodiment, the at least one tool further comprises a tip having a fluid channel in fluid communication with an inner portion of the at least one tool and on which a pipette is removably mountable. Preferably, the at least one tool further comprises a tip engageable with a cell manipulator and wherein the at least one energizeable unit comprises a motor for moving the manipulator when mounted on the tip. The cell manipulator can be a scraper, a knife or a tweezers.

In a still further embodiment, the at least one tool further comprises a reservoir and a tip having a channel in fluid communication with the reservoir and on which a pipette is removably mountable and wherein the at least one energizeable unit comprises a pump for outputting an amount of fluid from the reservoir and through the pipette when mounted on the tip. Alternatively, the at least one tool further comprises a tip having a channel in fluid communication with an internal portion of the at least one tool and on which a pipette is removably mountable and wherein the at least one energizeable unit comprises a pump for outputting an amount of fluid through the pipette when mounted on the tip.

In a further embodiment, the at least one tool further comprises a tip having and on which a cell picker is removably mountable and wherein the at least one energizeable unit comprises a vacuum pump for inputting a cell through the cell picker when mounted on the tip or for removing fluid through a pipette mounted on the tip.

In another embodiment, the at least one energizable unit comprises at least one sensor. The at least one sensor preferably senses at least one of pH, salts, minerals, temperature, electrical energy, and electromagnetic energy. Alternatively, the at least one sensor comprises an optic sensor which is preferably an imager. As a further alternative, at least one sensor comprises an electrical sensor which preferably senses at least capacitively, inductively, or electromagnetically.

In a still another embodiment, the at least one energizable unit comprises a radiator of plasma energy. Alternatively, the at least one energizable unit comprises a radiator of ultrasonic energy or a radiator of light. The light is preferably fluorescent light or ultraviolet light.

In a further embodiment, the at least one tool further comprises a reservoir and a tip having a channel in fluid communication with the reservoir and on which a pipette is removably mountable and wherein the at least one energizeable unit comprises a pump for outputting a sterilizing gas through the pipette when mounted on the tip. Alternatively, the at least one tool further comprises a reservoir for holding a compressed gas and a tip having a channel in fluid communication with the reservoir and on which a pipette is removably mountable and wherein the at least one energizeable unit comprises a valve for permitting the compressed gas to be output through the pipette when mounted on the tip. Preferably, the compressed gas is selected from the group consisting of oxygen, carbon dioxide, nitric oxide, carbon monoxide, hydrogen sulfide, sulfur dioxide, hydrogen cyanide, ammonia, methane, hydrogen, ethylene, and nitrous oxide.

In another embodiment, the at least one tool is removably mounted on the mandrel by one or more of a friction fit, a screw on connection, a mechanical latch or an electromagnetic connection.

These and other features of the present invention will be described in more detail with respect to the following drawing wherein:

BRIEF DESCRIPTION OF THE DRAWINGS

FIG. 5 is a perspective view of another embodiment of a tool in accordance with the present invention;

FIG. 6 is an inside view of the tool of FIG. 5;

FIG. 7 is a side view of a modification to the mandrel of FIGS. 1 and 2 to connect to the tool of FIGS. 6 and 7;

FIG. 8 is a scraper for connection to the tool of FIGS. 5 and 6;

FIG. 13 shows a circuit with alternative sources of power and control signals for a tool.

DETAILED DESCRIPTION OF THE PREFERRED EMBODIMENTS

Figure 2:
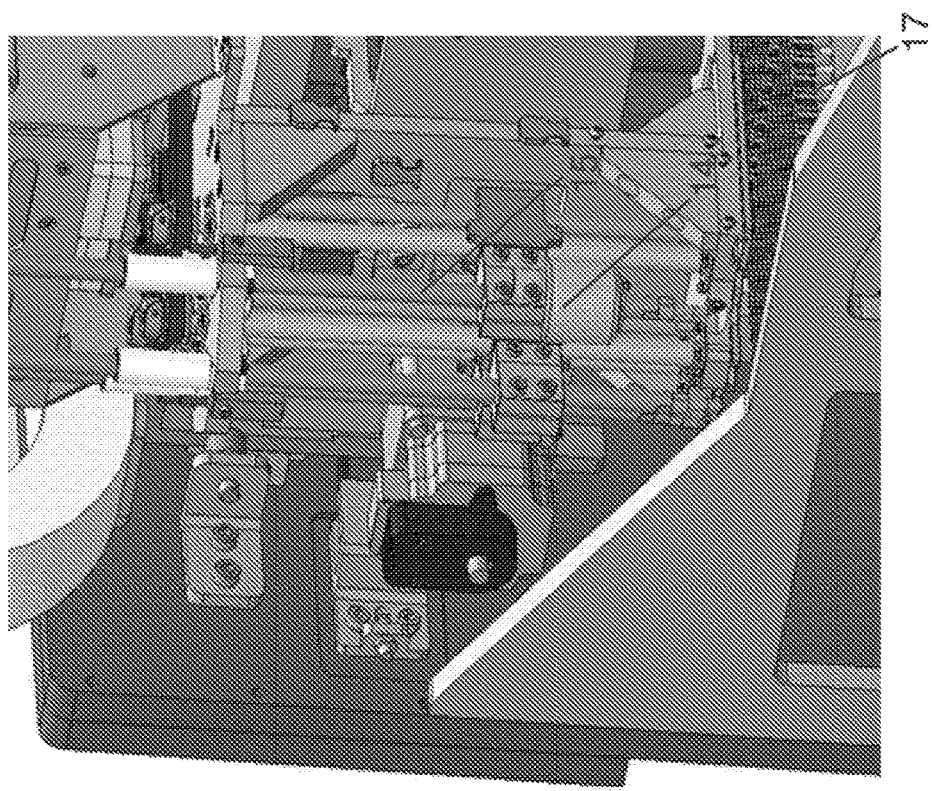
FIG. 2 is an enlarged view of a portion of FIG. 1.
Figure 1:
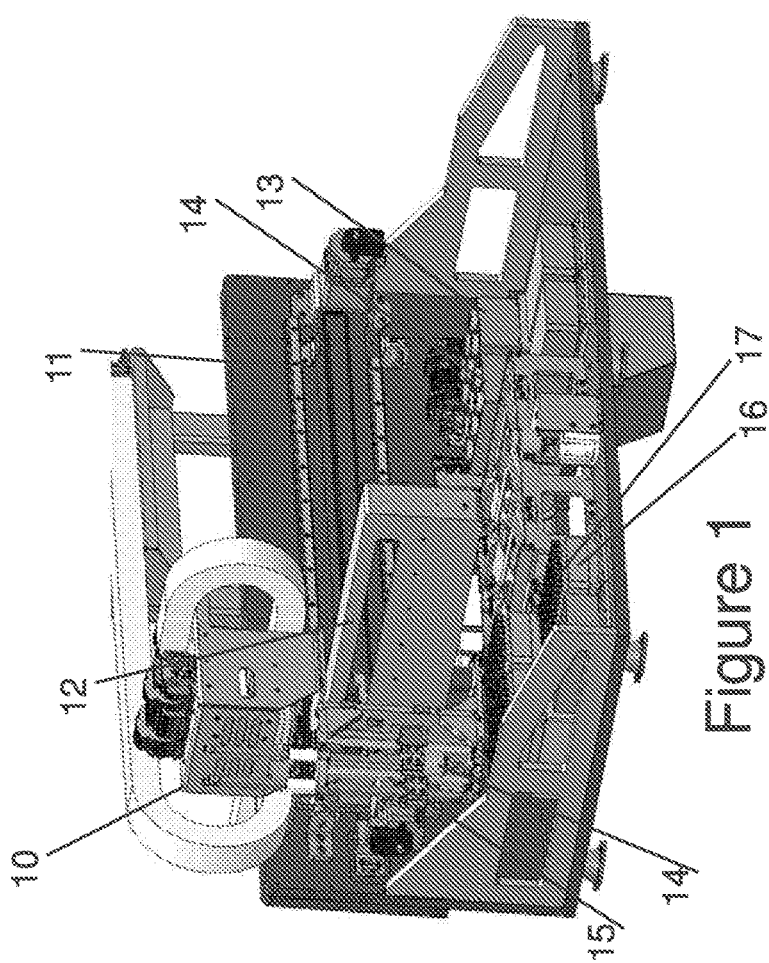
FIG. 1 is a perspective view of a cell incubator in which the present invention will operate.

As shown in FIGS. 1 and 2, the cell incubator designed by the applicant herein comprises a transport mechanism 10 that has X and Y axis tracks 11 and 12 that permit the transport mechanism to mode to any desired location in the X-Y plane. The transport mechanism carries mandrels 15 which the transport mechanism can move in the Z axis. A cell incubator of this type is made by Thrive Biosciences Corporation. Additional details relating to the type of cell incubator that the present invention is used in as well as the cell incubation processes and procedures in which the present invention can be used are disclosed in pending applications PCT/US2016/025362 filed Mar. 31, 2016, PCT/US2016/025356 filed Mar. 31, 2016, PCT/US2016/025349 filed Mar. 31, 2016, PCT/US2016/025339 filed Mar. 31, 2016, PCT/US2016/60722 filed Nov. 4, 2016, PCT/US2016/060710 filed Nov. 4, 2016, and PCT/US2016/62725 filed Nov. 18, 2016, all of which are hereby incorporated by reference.

The transport mechanism moves the mandrel 15 to tool storage racks 13 where tools 14 in accordance with one embodiment of the present invention are stored. The mandrel engages with the top of the tool 14 by a press or friction fit and the transport mechanism moves the mandrel and tools to a station where pipettes 17 are stored in racks 16. The mandrel lowers the tool to engage the pipette in a press fit so that the combination can be used to perform an operation on cells.

Figure 3:
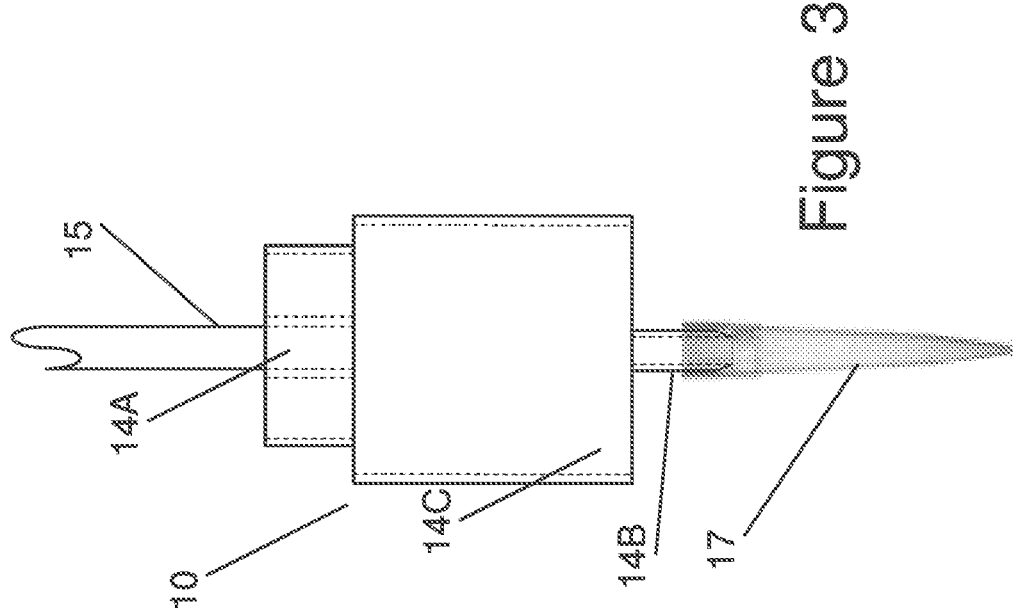
FIG. 3 is a side view of the tool used with the cell incubator of FIGS. 1 and 2 connected to a pipette.

The tool 14 is shown in more detail in FIG. 3. As shown, the tool 14 has a slot 14A at the top to receive the end of the mandrel 15 and a tip 14B at the bottom to connect to a pipette 17. The interior of the tool 14 is a reservoir 14C for liquids. The tool is preferably made from a high impact plastic material, although it can also be made from stainless steel or other metals.

Figure 4:
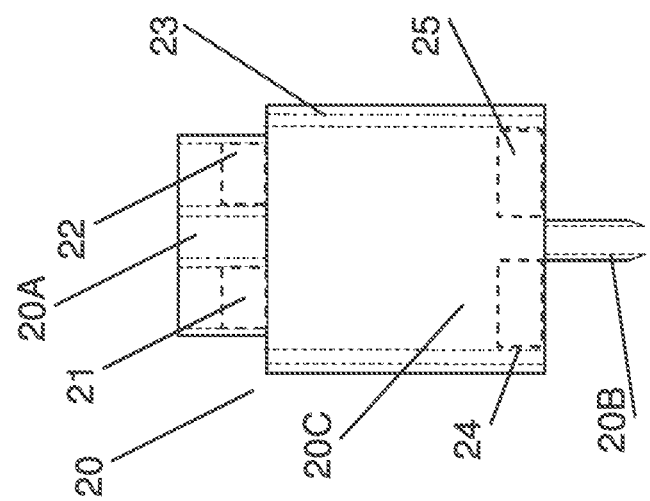
FIG. 4 is a side view of one embodiment of a tool in accordance with the present invention.

FIG. 4 shows one embodiment of an improved tool 20 according to the present invention. This tool has increased functionality due to the fact that it includes a rechargeable battery 23, a control circuit 21 which can preferably include a microprocessor and a wireless transceiver 22. The tool 20 also includes the slot 20A for engaging the mandrel 15 and the tip 20B for engaging a pipette and having a channel in fluid communication with a reservoir 20C. In addition, the tool 20 includes two units 24 and 25, each energizable by the battery 23 and controlled by the control circuit 21 based upon commands received at the wireless transceiver 22. For example, the wireless transceiver can be a Bluetooth transceiver with the antenna for the transceiver printed on the battery 23. The units 24 and 25 can be an imager and a light source for irradiating the area below the tool and for capturing an image of the irradiated area. The light source can be a laser diode, a fluorescent light, an ultraviolet light or any other light spectra which turns on genes in cells or running assays. The imager can be a two dimensional array such as those used in video cameras to detect a single image or a video image. Alternatively, the units 24 and 25 can be sensors of any type such as those detecting pH, salts, minerals and other substances.

As can be seen from FIG. 4, the tool 20 can be used in place of the existing tool 14 without modifying the incubator. In a preferred embodiment of the invention, the configuration of the tool 20 is the same as that of tool 14 so that it can be stored in racks 13 and does not prevent other tools from fitting on adjoining mandrels 15. The invention is not limited to a tool 20 having the same configuration as that of tool 14, particularly where a larger size for the tool 20 provides for increased functionality, for example the tool having multiple functions.

While the tool 20 is self-contained because it has its power supply and circuitry onboard, an alternative embodiment of the tool is shown in FIGS. 5 and 6. In this embodiment, the power supply and control circuit is in the incubator and the tool 30 includes a connector 31 with contacts for receiving power and control signals from the incubator through the connector contacts. The tool 30 also includes the slotted top portion 30A for engaging the mandrel and the tip 30B at the bottom for engaging a pipette. The interior of the tool 30 includes a reservoir 30C as well. In this embodiment, the mandrel 15 is fitted with an adapter 15A of FIG. 7 which carries a connector 15B that mates with connector 31 and supplies power and control signals when the bottom portion 15C of the mandrel engages the top 30A. The power and control signals are for motor 32 mounted in the tool 30 and which rotates tip 30B. This is particularly useful when scraper 18 shown in FIG. 8 is used. The top portion 18A of scraper 18 engages tip 30B and is rotated with it by motor 32 to improve the scraping function.

As can be seen in FIGS. 5 and 6, the tool 30 has a larger configuration than that of tool 14. However, the embodiment can also be configured to be the same size as tool 14 so that it can be stored in racks.

Figure 9:
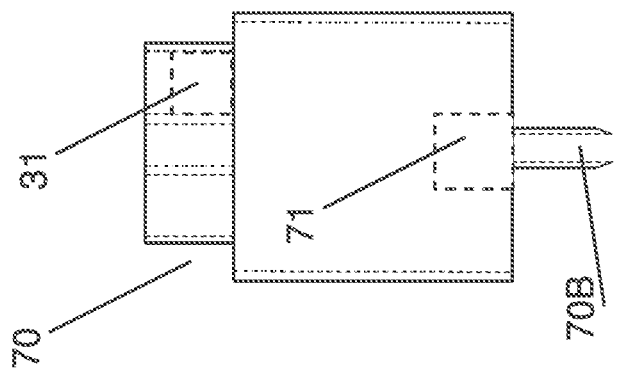
FIGS. 9-12 are alternative embodiments of the tools of FIGS. 4 and 5.

The tool with the contacts, rather than the built-in battery and control circuitry, can have the same energizable units therein as the embodiment of FIG. 4. For example, as shown in FIG. 9, the interior of the tool 40 includes a reservoir 40C and a micro-pump 41 which is powered by the power at the connector 31 controlled by the control signals through connecter 31 to deliver precise amounts of liquid or gas through the tip 40B into a pipette of other implement. For example, a tool 40 can be associated with a particular reagent which can be placed in the rack and picked up whenever that reagent is to be used.

Figure 10:
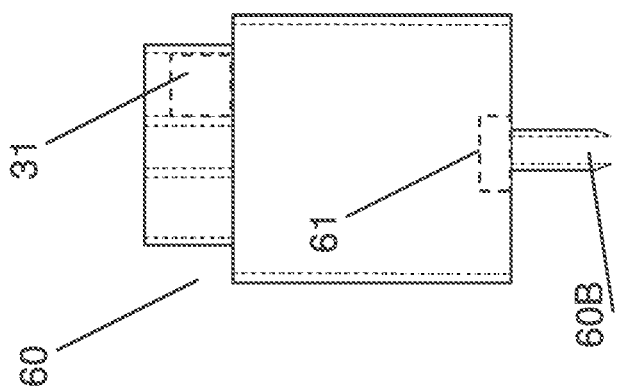
Figure 11:
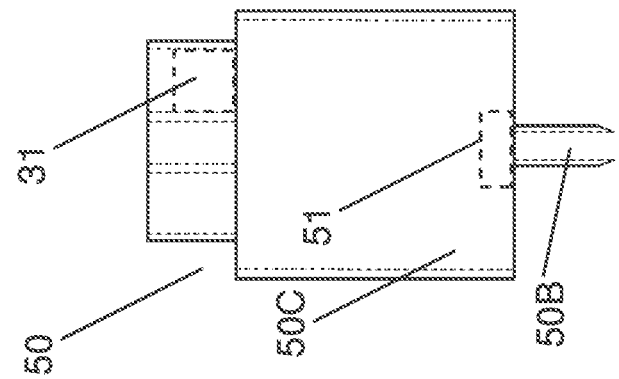
Figure 12:
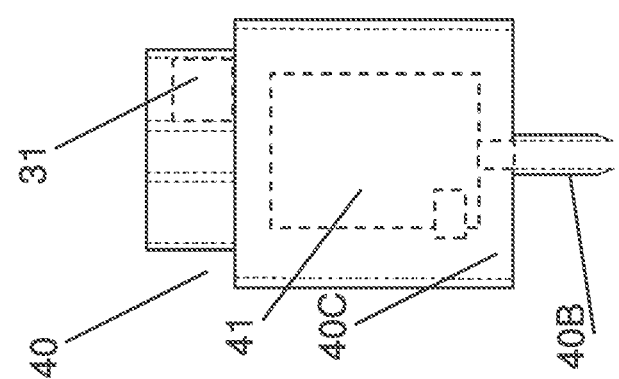

In the embodiment of FIG. 10, the reservoir 50C of tool 50 has a compressed gas stored therein and the unit 51 is a valve energized and controlled from power and signals through the connector 31. In the embodiment of FIG. 11, the unit 61 in tool 60 is an ultrasonic energy source. In the embodiment of FIG. 12, the unit 71 in tool 70 is an ozone gas generator. Alternatively, the unit can be a vacuum source for suction to remove fluid through a pipette tip or it can be a sensor for light, images or materials.

It should be understood that the various units referred to in conjunction with the embodiments of FIGS. 4-6 and 9-12 can be used in any of those embodiments and that the invention contemplates the use of one or multiple units in a tool. In addition, while the invention is shown using implements such as a pipette and a scraper, other implements such as a cell picker or cleaner.

FIG. 13 depicts alternative embodiments of the circuitry for a tool 20'. In one embodiment, the unit 25' within tool 20' receives control signals from a control circuit 21' which in turn receives inputs from a wireless transceiver 22', preferably a Bluetooth radio. The control circuit is preferably a microprocessor or a microcontroller, but may also be implemented by logic circuitry or an analog circuit. The transceiver 22' receives control signals from a wireless transceiver 2, preferably a Bluetooth radio, which is situated in the incubator external of the tool 20'. The transceiver 2 receives control signals from a microcontroller 1 situated in the incubator and externally of the tool 20'. While the circuit is depicted with a microcontroller, the circuit may be implemented with a microprocessor or logic circuitry. Power for the unit 25' is obtained from battery 23' in the toll 20'. Alternatively, the microcontroller 1 and the transceiver 2 can be external of the incubator as well. In another embodiment, the control circuit 21' includes a microprocessor and a memory which can be programmed to operate without external commands from the incubator. In this embodiment, data obtained from the cells being operated on would be processed by the software in the tool and control the operation of the tool. In a further embodiment, the tool can have a digital signature that is read by the incubator so that the function of the tool is automatically known to the incubator when attached to the mandrel.

In another embodiment, the unit 25' receives control signals from microcontroller 1 directly by means of contacts 31' mounted on the tool 20'. Additionally, power to the unit 25' comes from a power supply 3 situated in the incubator and external to the tool 20' via contacts 31'. Alternatively, the power supply 3 and the microcontroller 1 can be external to the incubator as well.

It is understood that while these embodiments are shown by way of example, the invention can use different combinations of the circuitry. For example, the unit 25' may be powered by a battery but receive is control signals from contacts 31'. In addition, the tools may receive its control signals via the transceiver 22' and control circuit 21', but receive power via the contacts 31'.

The invention, while shown using a press or friction fit for engaging the tool by a mandrel, it is understood that other techniques can be used within the scope of the invention, such as a screw on connection, a bayonet connection, a mechanical latch, or an electromagnetic engagement. In addition, it is understood that where a battery is included in the tool, a battery charger for the battery can be included in the storage rack for replenishing the battery.

While many tools have been described herein, the invention can adapt traditionally manual tools in a cell incubator. For example, many of those manual tools are described in the Fisher Scientific 2014/2016 catalog hereby incorporated by reference. The tools identified therein include, but are not limited to the cell culture equipment at pp. 260-261 and 279-280, scalpels at pp. 491-492 the measuring equipment at pp. 494-517, the electrodes at pp. 518-541, filters at pp. 602-618, forceps at p. 716, gauges at p. 790, meters at pp. 845-852, lights at pp. 887-888 and pp. 1546-7, microbiology and microchemistry tools at pp. 920-926, pipettes at pp. 1057-1166, pumps at pp. 1209-1230, samplers 1353-1356, scissors at pp. 1357-1358, shakers at pp. 1361-1394, and thermometers at pp. 1447-1473.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures and configurations, but the desired features can be implemented using a variety of alternative architectures and configurations. Indeed, it will be apparent to one of skill in the art how alternative functional, logical, or physical partitioning and configurations can be implemented to implement the desired features of the present disclosure. Additionally, with regard to operational descriptions, the order in which the steps are presented herein shall not mandate that the steps of the various embodiments be implemented in the order presented, unless the context dictates otherwise.

Although the disclosure is described above in terms of various example embodiments and implementations, it should be understood that the various features, aspects, and functionality described in one or more of the individual embodiments are not limited in their applicability to the particular embodiment with which they are described, but instead can be applied, alone or in various combinations, to one or more of the other embodiments of the disclosure, whether or not such embodiments are described, and whether or not such features are presented as being a part of a described embodiment. Thus, the breadth and scope of the present disclosure should not be limited by any of the above-described example embodiments, and it will be understood by those skilled in the art that various changes and modifications to the previous descriptions may be made within the scope of the claims.

What is claimed is:

1. A cell incubator comprising: a housing for holding a culture vessel, at least one mandrel having an end portion, the at least one mandrel mounted on a movable transport for moving the at least one mandrel relative to the culture vessel; and at least one tool removably mountable on the end portion of the at least one mandrel, wherein the at least one tool is electrically powered and controllable by signals applied to the at least one tool to perform at least one operation on cells in or from the culture vessel and wherein the at least one tool includes electrical contacts for mating with contacts on the at least one mandrel for receiving at least one of electrical energy and control signals and an energizable pump receiving at least one of the electrical energy and control signals from the contacts for performing an operation related to the incubation of cells.

2. The cell incubator according to claim 1, wherein the at least one tool further comprises a battery electrically connected to the energizable pump, said battery being for providing electrical energy to the energizable pump for performing an operation related to the incubation of cells and a control circuit for applying control signals to the energizable pump to control the operation of the energizable pump.

3. The cell incubator according to claim 2, wherein the at least one tool further comprises a wireless receiver for receiving control signals from externally of the at least one tool.

4. The cell incubator according to claim 1 or claim 2, wherein the transport moves at least one mandrel in an X-Y plane and moves the at least one mandrel along a Z-axis when a desired position is reached in the X-Y plane.

5. The cell incubator according to claim 1 or claim 2, wherein the at least one tool further comprises a tip having a fluid channel in fluid communication with an inner portion of the at least one tool and on which a pipette is removably mountable.

6. The cell incubator according to claim 1 or claim 2, wherein the at least one tool further comprises a tip engageable with a cell manipulator and wherein the at least one energizeable pump comprises a motor for moving the manipulator when mounted on the tip.

7. The cell incubator according to claim 6, wherein the cell manipulator is a scraper, a knife or tweezers.

8. The cell incubator according to claim 1 or claim 2, wherein the at least one tool further comprises a reservoir and a tip having a channel in fluid communication with the reservoir and on which a pipette is removably mountable and wherein the energizeable pump outputs an amount of fluid from the reservoir and through the pipette when mounted on the tip.

9. The cell incubator according to claim 1 or claim 2, wherein the at least one tool further comprises a tip having a channel in fluid communication with an internal portion of the at least one tool and on which a pipette is removably mountable and wherein the energizeable pump outputs an amount of fluid through the pipette when mounted on the tip.

10. The cell incubator according to claim 1 or claim 2, wherein the at least one tool further comprises a tip having and on which a cell picker is removably mountable and wherein the energizeable pump comprises a vacuum pump for inputting a cell through the cell picker when mounted on the tip.

11. The cell incubator according to claim 1 or claim 2, wherein the at least one tool further comprises at least one sensor.

12. The cell incubator according to claim 11, wherein the at least one sensor senses at least one of pH, salts, minerals, temperature, electrical energy, and electromagnetic energy.

13. The cell incubator according to claim 11, wherein the at least one sensor comprises an optic sensor.

14. The cell incubator according to claim 13, wherein the optic sensor comprises an imager.

15. The cell incubator according to claim 11, wherein the at least one sensor comprises an electrical sensor.

16. The cell incubator according to claim 12, wherein the electrical sensor senses at least capacitively, inductively, or electromagnetically.

17. The cell incubator according to claim 1 or claim 2, wherein the at least one tool further comprises a radiator of plasma energy.

18. The cell incubator according to claim 1 or claim 2, wherein the at least one tool further comprises a radiator of ultrasonic energy.

19. The cell incubator according to claim 1 or claim 2, wherein the at least one tool further comprises a radiator of light.

20. The cell incubator according to claim 19, wherein the light is fluorescent light.

21. The cell incubator according to claim 19, wherein the light is ultraviolet light.

22. The cell incubator according to claim 1 or claim 2, wherein the at least one tool further comprises a reservoir and a tip having a channel in fluid communication with the reservoir and on which a pipette is removably mountable and wherein the energizeable a pump outputs a sterilizing gas through the pipette when mounted on the tip.

23. The cell incubator according to claim 1 or claim 2, wherein the at least one tool further comprises a reservoir for holding a compressed gas and a tip having a channel in fluid communication with the reservoir and on which a pipette is removably mountable and wherein the energizeable pump comprises a valve for permitting the compressed gas to be output through the pipette when mounted on the tip.

24. The cell incubator according to claim 22, wherein the compressed gas is selected from the group consisting of oxygen, carbon dioxide, nitric oxide, carbon monoxide, hydrogen sulfide, sulfur dioxide, hydrogen cyanide, ammonia, methane, hydrogen, ethylene, and nitrous oxide.

25. The cell incubator according to claim 1, wherein the at least one tool is removably mounted on the at least one mandrel by one of a friction fit, a screw on connection, a mechanical latch or an electromagnetic connection.

26. The cell incubator according to claim 23, wherein the compressed gas is selected from the group consisting of oxygen, carbon dioxide, nitric oxide, carbon monoxide, hydrogen sulfide, sulfur dioxide, hydrogen cyanide, ammonia, methane, hydrogen, ethylene, and nitrous oxide.

* * * * *